US011141096B2

(12) United States Patent
Yamaoka et al.

(10) Patent No.: US 11,141,096 B2
(45) Date of Patent: Oct. 12, 2021

(54) METHOD FOR PREDICTING FUTURE CHANGE IN PHYSICAL CONDITION OF PERSON FROM SLEEP-STATE HISTORY

(71) Applicant: Panasonic Intellectual Property Corporation of America, Torrance, CA (US)

(72) Inventors: Masaru Yamaoka, Osaka (JP); Toshiaki Tanaka, Hyogo (JP); Kenji Masuda, Osaka (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 192 days.

(21) Appl. No.: 16/048,492

(22) Filed: Jul. 30, 2018

(65) Prior Publication Data
US 2019/0059802 A1 Feb. 28, 2019

Related U.S. Application Data

(60) Provisional application No. 62/550,835, filed on Aug. 28, 2017.

(30) Foreign Application Priority Data

Nov. 10, 2017 (JP) .............................. JP2017-217590
Apr. 25, 2018 (JP) .............................. JP2018-084150

(51) Int. Cl.
*A61B 5/00* (2006.01)
*A61B 5/01* (2006.01)
*A61B 5/11* (2006.01)

(52) U.S. Cl.
CPC .............. *A61B 5/4088* (2013.01); *A61B 5/01* (2013.01); *A61B 5/11* (2013.01); *A61B 5/4809* (2013.01); *A61B 5/7246* (2013.01); *A61B 5/7275* (2013.01)

(58) Field of Classification Search
CPC ........... A61B 5/4088; A61B 5/01; A61B 5/11; A61B 5/4809; A61B 5/7246; A61B 5/7275

(58) Field of Classification Search
USPC ......................................................... 600/549
See application file for complete search history.

(56) References Cited

U.S. PATENT DOCUMENTS

| | | | |
|---|---|---|---|
| 2002/0005784 A1* | 1/2002 | Balkin | G16H 15/00 340/573.1 |
| 2011/0295083 A1* | 12/2011 | Doelling | A61B 5/11 600/301 |

FOREIGN PATENT DOCUMENTS

| | | |
|---|---|---|
| JP | 5-003873 | 1/1993 |
| JP | 2013-150660 | 8/2013 |
| JP | 2016-022310 | 2/2016 |

* cited by examiner

*Primary Examiner* — May A Abouelela
*Assistant Examiner* — Chanel J Jhin
(74) *Attorney, Agent, or Firm* — Wenderoth, Lind & Ponack, L.L.P.

(57) ABSTRACT

A method includes: acquiring body motion data related to body motions of a target person; generating, based on the body motion data, sleep state data related to a sleep state of the target person; storing the sleep state data into a sleep state database; predicting a future change in a physical condition of the target person from the sleep state data by referencing a physical condition prediction information database; and when the physical condition data indicating the physical condition of the target person is acquired, reading past sleep state data over a past period from the sleep state database, collating the physical condition data with the past sleep state data to generate physical condition prediction information for predicting a particular change in the physical condition from particular sleep state data, and registering the physical condition prediction information into the physical condition prediction information database.

14 Claims, 9 Drawing Sheets

FIG. 7

| DATE | 9/7 | 9/8 | 9/9 | 9/10 | 9/11 | 9/12 | 9/13 | 9/14 | 9/15 |
|---|---|---|---|---|---|---|---|---|---|
| PHYSICAL CONDITION | ○ | ○ | ○ | ○ | ○ | ○ | X | ○ | ○ |
| | 9/16 | 9/17 | 9/18 | 9/19 | 9/20 | 9/21 | 9/22 | 9/23 | 9/24 |
| | ○ | ○ | ○ | X | ○ | ○ | ○ | ○ | X |
| | 9/25 | 9/26 | 9/27 | 9/28 | 9/29 | 9/30 | 10/1 | 10/2 | |
| | ○ | ○ | ○ | X | ○ | ○ | X | ○ | |

FIG. 10

| DATE | 5/21 | 5/22 | 5/23 | 5/24 | 5/25 | 5/26 | 5/27 |
|---|---|---|---|---|---|---|---|
| DAYTIME NAP COUNT | 2 | 1 | 1 | | | | |
| NOCTURNAL AWAKENING COUNT | 5 | 4 | 2 | 3 | 1 | 2 | 2 |
| NOCTURNAL AWAKENING TIME | 22:00 0:30 2:00 3:00-4:00 5:00-5:30 | 23:00 23:30 1:00 5:00 | 2:30 5:00-5:30 | 23:00 2:00 4:30-5:30 | 1:30-2:00 | 3:00 4:00 | 3:00-4:00 4:30-5:00 |
| NIGHT-TIME BEHAVIOR | WANDERING | DEMENTIA (DELUSION) | | | | | DEMENTIA (DELUSION) |

METHOD FOR PREDICTING FUTURE CHANGE IN PHYSICAL CONDITION OF PERSON FROM SLEEP-STATE HISTORY

BACKGROUND

1. Technical Field

The present disclosure relates to a method, an apparatus, and a program for predicting the physical condition of a target person.

2. Description of the Related Art

Appropriate physical condition management has been applied to a subject by monitoring daily sleep states obtained by a physical condition management system including a sleep sensor attached to the subject and an information terminal for analyzing measured data acquired by the sleep sensor (refer to, for example, Japanese Unexamined Patent Application Publication No. 2013-150660).

The sleep sensor described in Japanese Unexamined Patent Application Publication No. 2013-150660 analyzes the sleep state of a subject from the data measured by the sleep sensor and drives a display unit or a loudspeaker. In addition, according to Japanese Unexamined Patent Application Publication No. 2013-150660, an electric curtain, an audio device, a lighting device, a television set, an air conditioner, bedding (e.g., an electric bed or an air mat) are controlled in accordance with the sleep state of the subject determined by using the sleep sensor.

SUMMARY

In one general aspect, the techniques disclosed here feature a method including (A) continuously or intermittently acquiring body motion data related to body motions of a target person, (B) generating, based on the body motion data, sleep state data related to a sleep state of the target person, (C) storing the sleep state data into a sleep state database, (D) predicting a future change in a physical condition of the target person from the sleep state data by referencing a physical condition prediction information database, and (E) when the physical condition data indicating the physical condition of the target person is acquired, (e1) reading past sleep state data over a past period from the sleep state database, (e2) collating the physical condition data with the past sleep state data to generate physical condition prediction information for predicting a particular change in the physical condition from particular sleep state data, and (e3) registering the physical condition prediction information into the physical condition prediction information database.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 illustrates an example of physical condition data for a predetermined period;

FIG. 10 illustrates a correlation between the onset of the behavioral and psychological symptoms of dementia (BPSD) and a sleep state.

DETAILED DESCRIPTION

Figure 1:
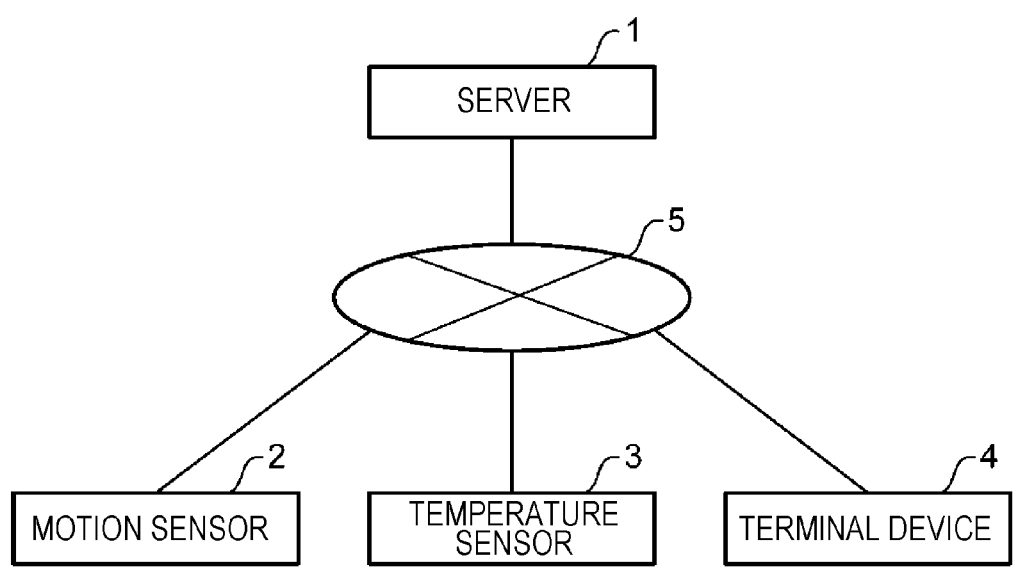
FIG. 1 is a block diagram illustrating an example of the configuration of a physical condition prediction system according to an embodiment of the present disclosure.

Underlying Knowledge Forming Basis of the Present Disclosure

In existing technology, drive control of a display unit or a loudspeaker incorporated into a sleep sensor is performed in accordance with the sleep state of a subject, and home electric appliances disposed outside the sleep sensor are remotely controlled.

For example, an existing home electric appliance control system can open an electric curtain, play music from audio device as an alarm, turn on a lighting device, tune a news channel on TV, set the bedroom temperature to an appropriate one by an air conditioner, and adjust the bedding so that the subject can easily wake up (e.g., make reclining adjustment of an electric bed or pressure adjustment of an air mat). As described above, according to the existing technique, cooperation between a sleep sensor and a variety of home electric appliances provides the subject a comfortable awakening.

However, although the existing technique describes that the devices are controlled in accordance with the sleep state of the subject analyzed by the sleep sensor, prediction of a change in the physical condition of the subject is not described.

According to an aspect of the present disclosure, a physical condition prediction method includes acquiring the biometric data of a target person, constantly determining the sleep state of the target person on the basis of the acquired biometric data, and predicting a change in the physical condition of the target person on the basis of the determined sleep state.

According to the configuration, the biometric data of the target person is acquired. The sleep state of the target person is constantly determined on the basis of the acquired biometric data. A change in the physical condition of the target person is predicted on the basis of the determined sleep state.

In this manner, a change in the physical condition of the target person can be predicted on the basis of the sleep state that is determined constantly. In addition, since a change in the physical condition of the target person is predicted, the care plan for the target person who is an elderly or a dementia patient, for example, can be readjusted and, thus, the target person can be assisted more efficiently.

In addition, in the above-described physical condition prediction method, the biometric data may include body motion data indicating the body motion of the target person and, in the determining, the sleep state may be constantly determined on the basis of the body motion data.

According to the configuration, the biometric data includes body motion data indicating the body motion of the target person. In the determining, the sleep state is constantly determined on the basis of the body motion data. Therefore, since the sleep state is always determined on the basis of the body motion data indicating the body motion of the target person, the sleep state of the target person can be accurately determined.

According to the above-described physical condition prediction method, if the body motion data falls below a predetermined value within a predetermined period of time, a decline in physical condition of the target person may be predicted in the predicting.

According to the configuration, in the predicting, if the body motion data falls below a predetermined value within a predetermined period, a decline in physical condition of the target person is predicted. Thus, a decline in physical condition of the target person can be reliably predicted from the body motion data.

In addition, according to the above-described physical condition prediction method, physical condition data indicating whether the physical condition of the target person is good or not may be further acquired, and a change in the physical condition may be predicted on the basis of a correlation between the history of the determined sleep state and the history of the acquired physical condition data.

According to the configuration, the physical condition data indicating whether the physical condition of the target person is good is acquired. In the predicting, a change in the physical condition is predicted from the correlation between the history of the determined sleep state and the history of the acquired physical condition data.

Therefore, if there is a correlation between the history of the sleep state and the history of the physical condition data, a change in the physical condition of the target person can be easily predicted by using the correlation.

In addition, according to the above-described physical condition prediction method, the body temperature of the target person may be further detected, and it may be further determined whether the body temperature of the target person is higher than a predetermined temperature. If it is determined that the body temperature is higher than the predetermined temperature, a decline in physical condition of the target person may be predicted.

According to the configuration, the body temperature of the target person is detected. It is determined whether the body temperature of the target person is higher than a predetermined temperature. If it is determined that the body temperature is higher than the predetermined temperature, a decline in physical condition of the target person is predicted.

Therefore, if it is determined that the body temperature of the target person is higher than the predetermined temperature, a decline in physical condition of the target person is predicted. As a result, a change in the physical condition of the target person can be easily predicted by using the body temperature of the target person.

According to the above-described physical condition prediction method, in the predicting, a decline in the physical condition of the target person may be predicted on the basis of the frequency of nocturnal awakening of the target person.

According to the configuration, in the predicting, a decline in the physical condition of the target person is predicted on the basis of the frequency of nocturnal awakening of the target person. If the frequency of nocturnal awakening of the target person is high, the sleep rhythm of the target person may be deranged. Accordingly, a decline in physical condition of the target person can be reliably predicted on the basis of the frequency of nocturnal awakening of the target person.

According to the above-described physical condition prediction method, in the predicting, if the frequency of nocturnal awakening of the target person is a predetermined number or more, a decline in physical condition of the target person may be predicted.

According to the configuration, since a decline in physical condition of the target person is predicted if the frequency of nocturnal awakening of the target person is a predetermined number or more in the predicting, a decline in physical condition of the target person can be reliably predicted.

In addition, according to the above-described physical condition prediction method, the decline in physical condition of the target person may include the onset of the behavioral and psychological symptoms of dementia. In the predicting, the onset of the behavioral and psychological symptoms of dementia of the target person may be predicted on the basis of at least one of the frequency of nocturnal awakening of the target person and the frequency of a nap of the target person during the daytime or in the evening.

According to the configuration, a decline in physical condition of the target person includes the onset of the behavioral and psychological symptoms of dementia. In the predicting, the onset of the behavioral and psychological symptoms of dementia of the target person is predicted on the basis of at least one of the frequency of nocturnal awakening of the target person and the frequency of a nap of the target person during the daytime or in the evening.

Accordingly, the onset of the behavioral and psychological symptoms of dementia of the target person can be reliably predicted on the basis of at least one of the frequency of nocturnal awakening of the target person and the frequency of a nap of the target person during the daytime or in the evening.

According to the above-described physical condition prediction method, in the predicting, a decline in physical condition of the target person may be predicted on the basis of the amount of time the target person is awake at night.

According to the configuration, a decline in the physical condition of the target person is predicted on the basis of the amount of time the target person is awake at night. If the amount of time the target person is awake at night is large, the sleep rhythm of the target person may be deranged. Thus, a decline in the physical condition of the target person can be reliably predicted on the basis of the amount of time the target person is awake at night.

According to the above-described physical condition prediction method, in the predicting, if the amount of time the target person is awake at night is greater than a predetermined amount of time, a decline in the physical condition of the target person may be predicted.

According to the configuration, in the predicting, since a decline in the physical condition of the target person is predicted if the amount of time the target person is awake at night is a predetermined amount of time or more, a decline in physical condition of the target person can be reliably predicted.

In addition, according to the above physical condition prediction method, a prediction result predicting a change in the physical condition of the target person may be transmitted to the terminal device.

According to the configuration, since the prediction result predicting the change in the physical condition of the target person is transmitted to the terminal device, a manager can be notified of the prediction result through the terminal device.

According to another aspect of the present disclosure, a physical condition prediction apparatus includes a communication unit and a processor. The communication unit acquires the biometric data of a target person, and the processor constantly determines the sleep state of the target person on the basis of the acquired biometric data of the target person and predicts a change in the physical condition of the target person on the basis of the determined sleep state.

According to the configuration, the biometric data of the target person is acquired. The sleep state of the target person is constantly determined on the basis of the acquired biometric data. A change in the physical condition of the target person is predicted on the basis of the determined sleep state.

In this manner, a change in the physical condition of the target person can be predicted on the basis of the sleep state that is determined constantly. In addition, since a change in the physical condition of the target person is predicted, the care plan for the target person who is an elderly or a dementia patient, for example, can be readjusted and, thus, the target person can be assisted more efficiently.

According to still another aspect of the present disclosure, a physical condition prediction program causes a processor to constantly determine the sleep state of a target person on the basis of the biometric data of the target person and to perform a process to predict a change in the physical condition of the target person on the basis of the determined sleep state.

According to the configuration, the sleep state of the target person is constantly determined on the basis of the biometric data of the target person. A change in the physical condition of the target person is predicted on the basis of the determined sleep state.

In this manner, a change in the physical condition of the target person can be predicted on the basis of the sleep state that is determined constantly. In addition, since a change in the physical condition of the target person is predicted, the care plan for the target person who is an elderly or a dementia patient, for example, can be readjusted so that the target person can be assisted more efficiently.

Embodiments according to the present disclosure are described below with reference to the accompanying drawings. It should be noted that the following embodiments are merely specific examples of the present disclosure and do not limit the technical scope of the present disclosure.

Embodiment

FIG. 1 is a block diagram illustrating an example of the configuration of a physical condition prediction system according to an embodiment of the present disclosure. As illustrated in FIG. 1, the physical condition prediction system includes a server 1, a motion sensor 2, a temperature sensor 3, and a terminal device 4.

The server 1 is connected to the motion sensor 2, the temperature sensor 3, and the terminal device 4 via a network 5 for communication. The network 5 is, for example, the Internet.

The motion sensor 2 is, for example, a Doppler sensor. The motion sensor 2 is installed on the ceiling or the wall of the room of the target person. The target person is, for example, a resident of an elderly residential home and is an elderly person or a care receiver. The motion sensor 2 emits radio waves and compares the frequency of the radio wave reflected by the target person with the frequency of the emitted radio waves. In this manner, the motion sensor 2 detects the motion of the target person. The motion sensor 2 constantly detects the body motion of the target person and constantly transmits, to the server 1, body motion data indicating the detected body motion of the target person. It is desirable that the motion sensor 2 continuously detect the body motion of the target person at 1-second intervals, for example. However, the motion sensor 2 may continuously detect the body motion of the target person at, for example, 1-minute intervals. The detection interval is not limited to a specific value. Body motion data is an example of biometric data. The motion sensor 2 can detect not only the body motion of the target person but also the pulse and respiration of the target person.

Note that the motion sensor 2 may be, for example, an acceleration sensor. In this case, the motion sensor 2 is worn on the body of the target person and detects the body motion of the target person.

Furthermore, the motion sensor 2 may be incorporated into a home electrical appliance, such as a lighting device disposed in a room.

The temperature sensor 3 is, for example, an infrared camera and is installed on the ceiling or the wall of the room of the target person. The temperature sensor 3 constantly captures the infrared image in the room and constantly transmits the captured infrared image to the server 1.

Note that the temperature sensor 3 may be incorporated into a home electric appliance, such as an air conditioner installed in a room.

The terminal device 4 is, for example, a personal computer or a tablet computer. The terminal device 4 is operated by an administrator who manages the physical condition of the target person. The terminal device 4 receives an input from the administrator of physical condition data indicating whether the physical condition of the target person is good or not. For example, the terminal device 4 receives an input of physical condition data indicating whether the physical condition of the target person is good or not on a daily basis. Note that the terminal device 4 may receive an input of physical condition data indicating whether the physical condition of the target person is good or not at predetermined time intervals or for every predetermined time zone. The terminal device 4 transmits the input physical condition data to the server 1.

Furthermore, in addition to receiving information as to whether the physical condition of the target person is good or not, the terminal device 4 may receive an input of other information. For example, the terminal device 4 may receive input of information about nursing care records, such as the type of medication administered to the target person and the administration time.

The motion sensor 2 and the temperature sensor 3 may directly transmit the sensing data to the server 1 or may transmit the sensing data to the server 1 via the terminal device 4.

Figure 2:
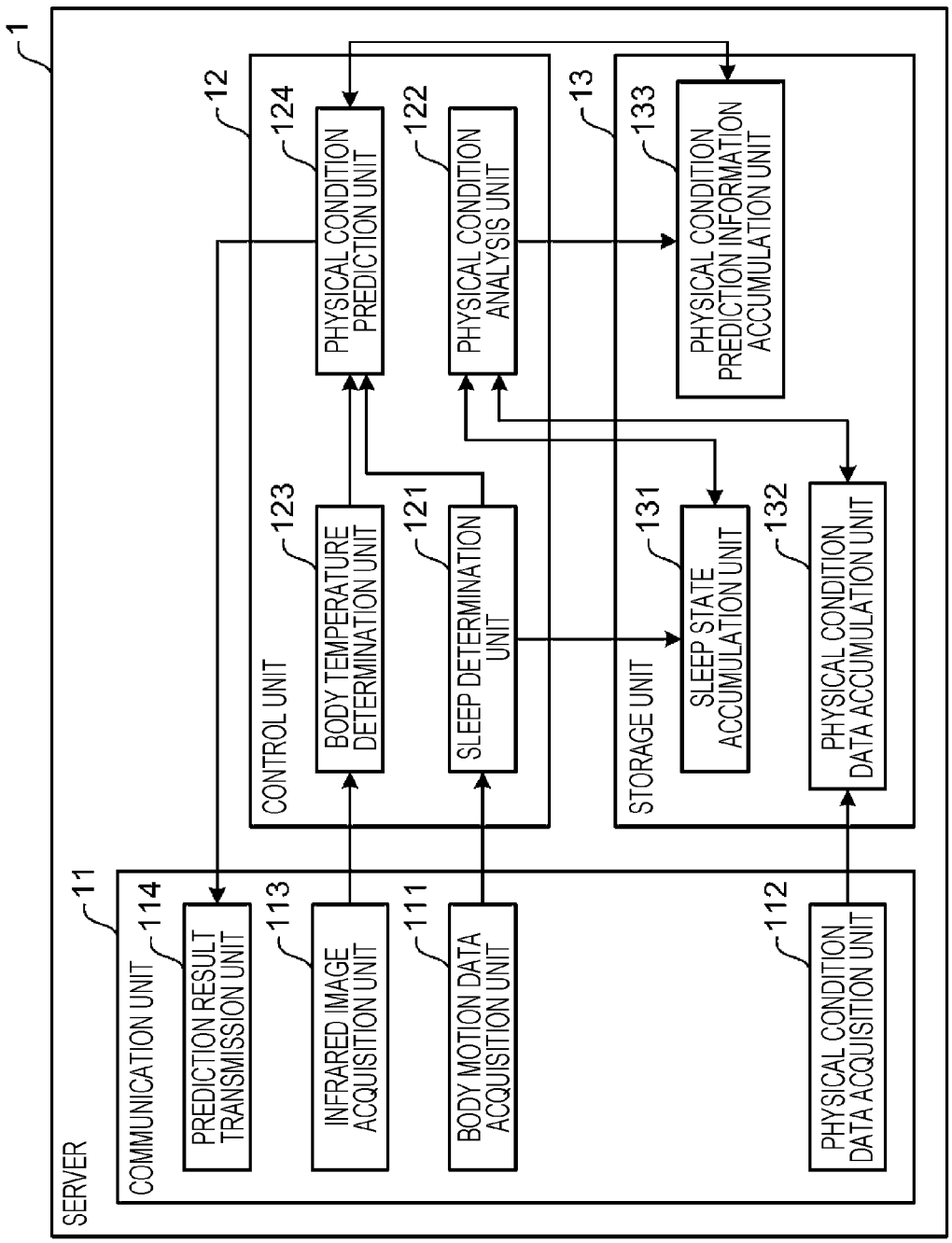
FIG. 2 is a block diagram illustrating an example of the configuration of a server illustrated in FIG. 1.

FIG. 2 is a block diagram illustrating an example of the configuration of the server 1 illustrated in FIG. 1. As illustrated in FIG. 2, the server 1 includes a communication unit 11, a control unit 12, and a storage unit 13.

The communication unit 11 includes a body motion data acquisition unit 111, a physical condition data acquisition unit 112, an infrared image acquisition unit 113, and a prediction result transmission unit 114.

The body motion data acquisition unit 111 acquires body motion data indicating the motion of the body of the target person. The body motion data acquisition unit 111 receives the body motion data transmitted from the motion sensor 2.

The body motion data acquisition unit 111 may acquire the body motion data transmitted from a body motion sensor. For example, the body motion data acquisition unit 111 may acquire a body motion value at 1-minute intervals.

The physical condition data acquisition unit 112 acquires physical condition data indicating whether the physical condition of the target person is good or not. The physical condition data acquisition unit 112 receives the physical condition data transmitted from the terminal device 4.

The physical condition data acquisition unit 112 may acquire information recorded by, for example, a care giver (e.g., the nursing care records). The physical condition information data includes, for example, vital signs, such as body temperature or blood pressure, observation records based on the subjective observation of the care giver, the presence or absence of a fall, and BPSD (e.g., wandering and delusions).

The infrared image acquisition unit 113 acquires an infrared image. The infrared image acquisition unit 113 receives the infrared image transmitted from the temperature sensor 3.

The control unit 12 is, for example, a central processing unit (CPU) and performs overall control of the server 1. The control unit 12 includes a sleep determination unit 121, a physical condition analysis unit 122, a body temperature determination unit 123, and a physical condition prediction unit 124.

The storage unit 13 is, for example, a semiconductor memory or a hard disk drive. The storage unit 13 includes a sleep state accumulation unit 131, a physical condition data accumulation unit 132, and a physical condition prediction information accumulation unit 133.

The sleep determination unit 121 constantly determines the sleep state of the target person on the basis of the body motion data acquired by the body motion data acquisition unit 111.

The sleep determination unit 121 may determine sleep/wakefulness on the basis of the body motion measured and acquired for 7 minutes by the body motion data acquisition unit 111. Note that sleep/wakefulness is determined on the basis of the Cole equation that is also used in medical devices (e.g., Actigraph). In addition, absolute time information is attached to the body motion data to be acquired.

The sleep state accumulation unit 131 accumulates the history of the sleep state of the target person determined by the sleep determination unit 121. The sleep state accumulation unit 131 accumulates information as to whether the target person is asleep or awake in units of a predetermined time period. The unit of predetermined time period is, for example, 1 minute or 1 second.

The sleep state accumulation unit 131 may accumulate information about sleep/wakefulness determined by the sleep determination unit 121 together with time information.

Figure 3:
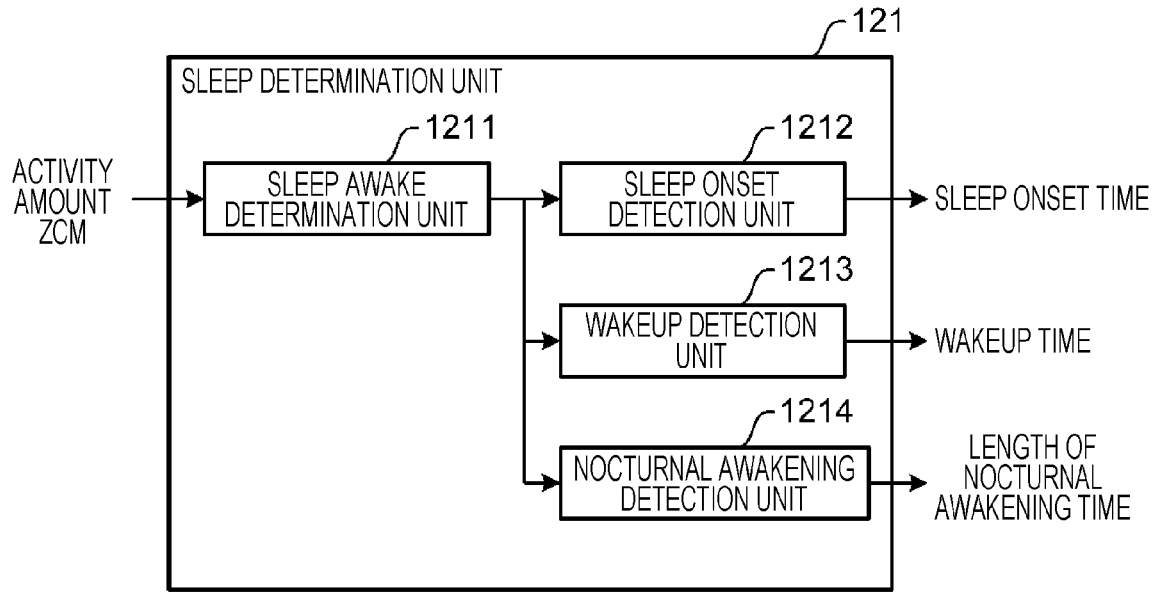
FIG. 3 illustrates the configuration of a sleep determination unit illustrated in FIG. 2.

FIG. 3 is a diagram illustrating the configuration of the sleep determination unit illustrated in FIG. 2. As illustrated in FIG. 3, the sleep determination unit 121 includes a sleep awake determination unit 1211, a sleep onset detection unit 1212, a wakeup detection unit 1213, and a nocturnal awakening detection unit 1214. The body motion data includes the activity amount (the magnitude of motion) ZCM for each 1-minute time period. The body motion data is input from the body motion data acquisition unit 111 to the sleep awake determination unit 1211.

The sleep awake determination unit 1211 calculates a determination value S by using the following equation (1):

$$S=0.0033(1.06ZCM_{-4min}+0.54ZCM_{-3min}+0.58ZCM_{-2min}+0.76ZCM_{-1min}+2.3ZCM_{now}+0.74ZCM_{+1min}+0.67ZCM_{+2min}) \quad (1),$$

where $ZCM_{-4min}$ represents the activity amount 4 minutes ago, $ZCM_{-3min}$ represents the activity amount three minutes ago, $ZCM_{-2min}$ represents the activity amount two minutes ago, $ZCM_{-1min}$ represents the amount of activity one minute ago, $ZCM_{now}$ represents the activity amount at the time of determination, $ZCM_{+1min}$ represents the activity amount after one minute, and $ZCM_{+2min}$ represents the activity amount after two minutes.

If the determination value S is 1 or greater, the sleep wake determination unit 1211 determines that the target person is awake. However, if the determination value S is less than 1, the sleep wake determination unit 1211 determines that the target person is asleep.

The sleep onset detection unit 1212 detects, as a sleep onset time at which the target person fell asleep, the start time of a period that was determined as a period in which the target person was continuously sleeping for a predetermined time or longer. The sleep onset detection unit 1212 outputs the detected sleep onset time to the sleep state accumulation unit 131 and the physical condition prediction unit 124.

The wakeup detection unit 1213 detects, as the wakeup time at which the target person woke up, the start time of a period that was determined as a period for which the target person was continuously awake for a predetermined period of time or longer. The wakeup detection unit 1213 outputs the detected wakeup time to the sleep state accumulation unit 131 and the physical condition prediction unit 124.

The nocturnal awakening detection unit 1214 detects the amount of time determined to be an amount of time the target person continuously stayed awake within the period from the sleep onset time to the wakeup time as the length of nocturnal awakening time. The nocturnal awakening detection unit 1214 outputs the detected length of nocturnal awakening time to the sleep state accumulation unit 131 and the physical condition prediction unit 124.

In addition to the sleep onset time, the wakeup time, and the length of nocturnal awakening time, the sleep determination unit 121 may output, to the sleep state accumulation unit 131, the result of the determination of sleep/wakefulness made by the sleep awake determination unit 1211 as a sleep state. In addition to the sleep onset time, the wakeup time, and the length of nocturnal awakening time, the sleep state accumulation unit 131 may accumulate, as the sleep state, a time change of sleep/wakefulness of the target person.

According to the present embodiment, the sleep awake determination unit 1211 calculates the determination value S by using the above-described equation (1). However, the present disclosure is not limited thereto. The determination value S may be calculated by using another equation, such as the following equation (2):

$$S=0.00001(404ZCM_{-4min}+598ZCM_{-3min}+326CM_{-2min}+441ZCM_{-1min}+1408ZCM_{now}+508ZCM_{+1min}+350ZCM_{+2min}) \quad (2).$$

The above-described equation (2) is known as Cole equation, which is a widely used equation for sleep determination (Roger J. Cole, Daniel F. Kripke, William Gruen, Daniel J. Mullaney, J. Christian Gillin, "Automatic Sleep/Wake Identification From Wrist Activity", 15 (5), 461-469, 1992). In the above-described equation (2), $ZCM_{-4min}$ represents the activity amount 4 minutes ago, $ZCM_{-3min}$ represents the activity amount three minutes ago, and $ZCM_{-2\ min}$ represents the activity amount two minutes ago, $ZCM_{now}$ represents the activity amount at the time of determination, $ZCM_{-1\ min}$ represents the amount of activity after one minute, and $ZCM_{+2\ min}$ represents the amount of activity after two minutes.

The physical condition data accumulation unit 132 accumulates the physical condition data acquired by the physical condition data acquisition unit 112. Like the sleep state accumulation unit 131, the physical condition data accumulation unit 132 may accumulate the physical condition data together with the information about the time at which the physical condition was recorded.

The physical condition analysis unit 122 analyzes the trends in the sleep state of the target person before a decline in physical condition of the target person occurs on the basis of a correlation between the physical condition data indicating whether the physical condition of the target person for the predetermined period is good or not and the sleep state of the target person for the predetermined period.

For example, the physical condition analysis unit 122 reads the physical condition data for the predetermined period from the physical condition data storage unit 132 and reads the sleep state for the predetermined period from the sleep state accumulation unit 131. The predetermined period is, for example, one month. The physical condition analysis unit 122 analyzes the physical condition data and the sleep state of the predetermined period. If sleep deprivation that lasts for two days results in a decline in physical condition, the physical condition analysis unit 122 generates physical condition predict information indicating that sleep deprivation that lasts for two days results in a decline in physical condition. Note that if the sleep duration measured between 7:00 p.m. and 7:00 a.m. is less than a predetermined time period, it is determined that sleep deprivation occurs. The physical condition analysis unit 122 accumulates the generated physical condition prediction information in the physical condition prediction information accumulation unit 133.

In addition, for example, the physical condition analysis unit 122 analyzes the physical condition data and the sleep state of one month. If the frequency of nocturnal awakening that occurs during sleep between the sleep onset time and the wakeup time is greater than or equal to a predetermined value on the day before the physical condition deteriorates, the physical condition analysis unit 122 generates the following physical condition prediction information: if the frequency of nocturnal awakening that occurs during sleep is greater than or equal to the predetermined value, the physical condition deteriorates on the following day.

Furthermore, for example, the physical condition analysis unit 122 analyzes the physical condition data and the sleep state of one month. If the total duration of nocturnal awakening that occurs during sleep between the sleep onset time and the wakeup time is greater than or equal to a predetermined value on the day before the physical condition deteriorates, the physical condition analysis unit 122 generates the following physical condition prediction information: if the total duration of nocturnal awakening that occurs during sleep is greater than or equal to the predetermined value, the physical condition deteriorates on the following day.

The physical condition analysis unit 122 may train a prediction model that predicts a decline in physical condition of the target person by using, as the teacher data, the physical condition data indicating whether the physical condition of the target person for the predetermined period is good or not and the sleep state of the target person for the predetermined period and inputting the teacher data to the prediction model. Thereafter, the physical condition analysis unit 122 may store the prediction model in the physical condition prediction information accumulation unit 133 as the physical condition prediction information.

The physical condition analysis unit 122 performs cross analysis between the sleep state obtained from the sleep state accumulation unit 131 and the physical condition data obtained from the physical condition data accumulation unit 132. The physical condition analysis unit 122 may extract incident information about the physical condition accumulated in the physical condition data accumulation unit 132. The incident information includes, for example, a fall and the time of the fall, fever and the time of the fever, and the onset of BPSD and the time of the onset of BPSD. In addition, when an incident occurs, the physical condition analysis unit 122 may extract the sleep state immediately before the time of the occurrence of incident. In this way, the physical condition analysis unit 122 may accumulate, in the physical condition prediction information accumulation unit 133, the sleep state or a body temperature change state immediately before the occurrence of incident for each of the types of the incident information to be extracted in accordance with the state of an elderly person.

The physical condition prediction information accumulation unit 133 accumulates the physical condition prediction information used to predict a change in the physical condition of the target person. Note that the correlation between the physical condition data and the sleep state varies person to person. Accordingly, the physical condition prediction information is information unique to the target person. The physical condition prediction information is stored in the physical condition prediction information accumulation unit 133 in association with the target person.

The body temperature determination unit 123 determines whether the body temperature of the target person is higher than a predetermined temperature on the basis of the infrared image acquired by the infrared image acquisition unit 113.

Figure 4:
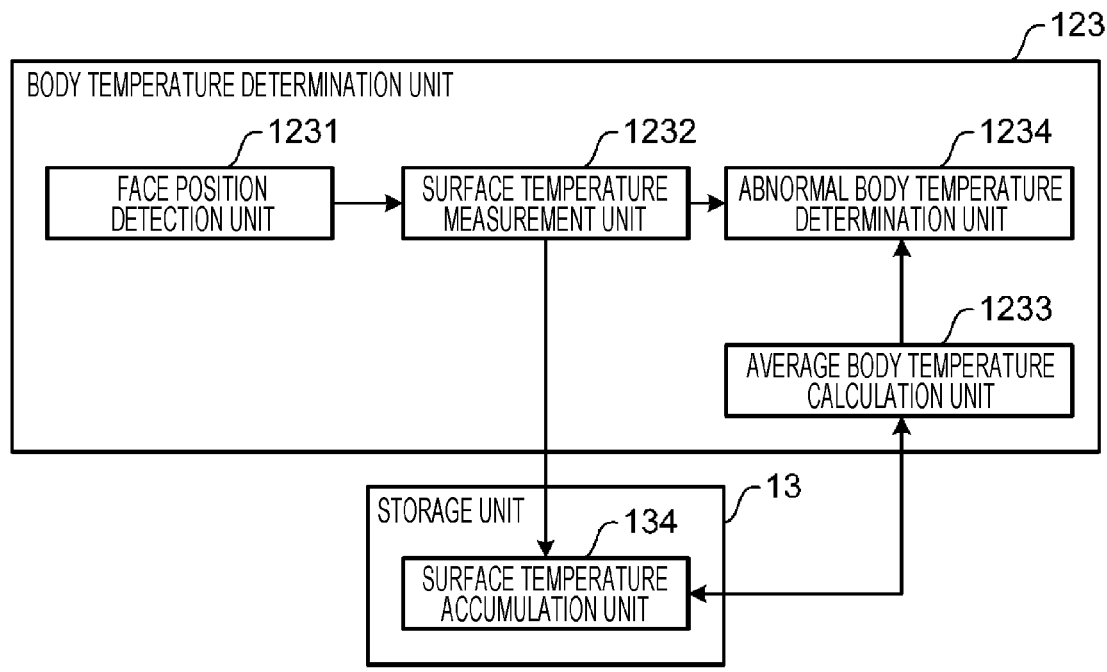
FIG. 4 illustrates the configuration of a body temperature determination unit illustrated in FIG. 2.

FIG. 4 illustrates the configuration of the body temperature determination unit 123 illustrated in FIG. 2. As illustrated in FIG. 4, the body temperature determination unit 123 includes a face position detection unit 1231, a surface temperature measurement unit 1232, an average body temperature calculation unit 1233, and an abnormal body temperature determination unit 1234. The storage unit 13 includes a surface temperature accumulation unit 134.

The face position detection unit 1231 detects the position of the face of the target person in the infrared image acquired by the infrared image acquisition unit 113. The face position detection unit 1231 detects the position of the face of the target person from the infrared image by, for example, pattern matching.

The surface temperature measuring unit 1232 measures the surface temperatures at the position of the face detected by the face position detection unit 1231.

The surface temperature accumulation unit 134 accumulates the surface temperature measured by the surface temperature measurement unit 1232 at the position of the face.

The average body temperature calculation unit 1233 calculates the average value of the surface temperatures at the position of the face accumulated in the surface temperature accumulation unit 134 as the average body temperature.

The abnormal body temperature determination unit 1234 determines whether the surface temperature at the position of the face measured by the surface temperature measurement unit 1232 is higher than the average body temperature calculated by the average body temperature calculation unit 1233. If the abnormal body temperature determination unit 1234 determines that the measured surface temperature at the position of the face is higher than the average body temperature, the abnormal body temperature determination unit 1234 determines that the body temperature of the target person is abnormal. However, if the abnormal body temperature determination unit 1234 determines that the measured surface temperature at the position of the face is lower than or equal to the average body temperature, the abnormal body temperature determination unit 1234 determines that the body temperature of the target person is normal.

The physical condition prediction unit 124 predicts a change in the physical condition of the target person on the basis of the sleep state determined by the sleep determination unit 121. The physical condition prediction unit 124 predicts a change in the physical condition from the correlation between the history of the sleep state determined by the sleep determination unit 121 and the history of the physical condition data acquired by the physical condition data acquisition unit 112.

The physical condition prediction unit 124 refers to the physical condition prediction information generated from the correlation between the sleep state obtained for a predetermined period of time and the physical condition data obtained for the predetermined period of time and accumulated in the physical condition prediction information accumulation unit 133. If the sleep state determined by the sleep determination unit 121 meets a condition defined by the physical condition prediction information, the physical condition prediction unit 124 predicts that the physical condition deteriorates. For example, the physical condition prediction unit 124 predicts that if the target person has total sleep duration less than a predetermined value per night for 2 straight days, the physical condition of the target person deteriorates on the following day.

Alternatively, the physical condition prediction unit 124 may predict a decline in physical condition of the target person on the basis of the frequency at which the target person awakens at night. That is, the physical condition prediction unit 124 may predict a decline in physical condition of the target person if the frequency at which the target person awakens at night is a predetermined value or more. For example, the physical condition prediction unit 124 may predict that the physical condition of the target person deteriorates on the following day if the frequency of nocturnal awakening at night is equal to or more than the predetermined value.

Still alternatively, the physical condition prediction unit 124 may predict a decline in physical condition of the target person on the basis of an amount of time the target person is awake at night. That is, if the amount of time the target person is awake at night is greater than or equal to a predetermined value, the physical condition prediction unit 124 may predict a decline in physical condition of the target person. For example, the physical condition prediction unit 124 may predict that the physical condition of the target person deteriorates on the following day if the total length of nocturnal awakening time during sleep at night is greater than or equal to a predetermined value.

In addition, if the body temperature determination unit 123 determines that the body temperature of the target person is higher than a predetermined temperature, the physical condition prediction unit 124 may predict a decline in physical condition of the target person.

In addition, the physical condition prediction unit 124 may perform the likelihood analysis (pattern matching) on the sleep state input from the sleep determination unit 121 in real time and the sleep states that are obtained at the time of incidents and that are accumulated in the physical condition prediction information accumulation unit 133. As a result of the likelihood analysis, the physical condition prediction unit 124 can obtain the likelihood between the input sleep pattern and the sleep pattern at the time of an incident and, thus, can predict a decline in physical condition by comparing the likelihood with a threshold value.

In this manner, the present system learns the typical sleep patterns or the typical body temperature change patterns that lead to a decline in physical condition as teacher data by using the physical condition data acquisition unit 112. As a result, the system can alert the occurrence of an incident that involves an elderly person and that cannot be predicted by the care giver.

In addition, while the present embodiment has been described with reference to the physical condition data acquisition unit 112 that acquires the past physical condition data of a person whose decline in physical condition is to be predicted, the physical condition data acquisition unit 112 is not limited thereto. For example, the physical condition data acquisition unit 112 may acquire the physical condition data of another person who has a similar past heath history or who has received care in a similar manner. In this case, the physical condition prediction unit 124 can predict the physical condition of a person on the basis of the physical condition data of another person.

Furthermore, while the present embodiment has been described with reference to the physical condition prediction unit 124 that performs likelihood analysis, the analysis performed by the physical condition prediction unit 124 is not limited thereto. For example, to detect abnormality in vital signs, the same effect can be obtained from probability analysis using a hidden Markov model or the like. Even when there is no observation record of a care giver (e.g., the nursing care record), probability analysis enables calculation of the probability of the occurrence of a similar incident (prediction) from the sleep state by obtaining an abnormal value of the vital signs and setting the occurrence of the abnormal value as an incident.

Furthermore, while the present embodiment has been described with reference to a physical condition predicted from the sleep state or the body temperature, a technique for prediction is not limited thereto. Basically, the sleep information used by the present system is calculated from the body motion of an elderly person, that is, the activity state of the elderly person. Therefore, the physical condition can be predicted by pattern analysis of the activity state of the elderly person and incidents. For example, it can be predicted that the activity amount has reduced due to a decline in physical condition or dehydration.

Note that even when the blood pressure, for example, is used as the vital sign instead of the body temperature, the same effects as described above can be obtained. In particular, in terms of the blood pressure, a wristwatch type sphygmomanometer has been put into commercial use recently. By using a sphygmomanometer of a wristwatch type, continuous blood pressure data can be obtained, and pattern analysis of a change in the blood pressure and incidents can be performed.

Furthermore, in the likelihood analysis performed by the physical condition prediction unit 124, correlation analysis based on deep learning or machine learning is available. In particular, in the case of elderly people, the incident information about the physical condition accumulated in the physical condition data accumulation unit 132 is complex information, in many cases. To detect a correlation between such complex information and the life rhythms, such as sleep, analysis for multiple correlations is needed. In addition, if, in addition to the data of the person, the data of other persons are taken into consideration, correlation analysis is more complicated. In this case, correlation analysis can be performed by using deep learning or machine learning.

The prediction result transmission unit 114 transmits, to the terminal device 4, the physical condition prediction result indicating a change in the physical condition of the target person. Upon predicting a decline in physical condition of the target person, the prediction result transmission unit 114 transmits the physical condition prediction result to the terminal device 4.

The terminal device 4 receives the physical condition prediction result transmitted from the server 1 and notifies a manager of the received physical condition prediction result. The terminal device 4 displays, for example, the received physical condition prediction result. In addition, for example, the terminal device 4 may output the received physical condition prediction result by voice. Note that the terminal device 4 for notifying the manager of the physical condition prediction result may be the same as or different from the terminal device that receives the input of the physical condition data.

Figure 5:
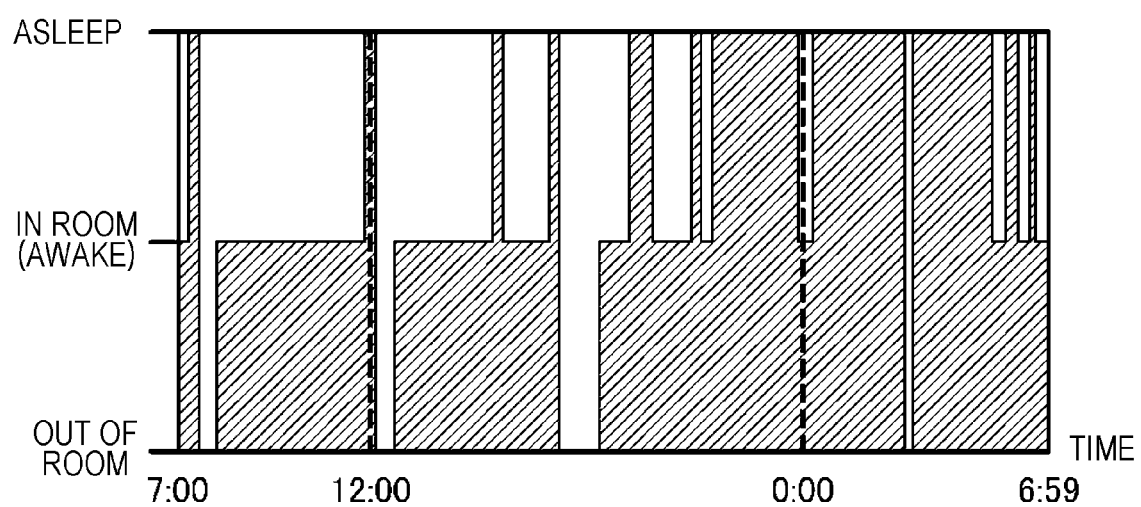
FIG. 5 illustrates an example of a sleep state for one day output from the sleep determination unit.

FIG. 5 illustrates an example of the sleep state output from the sleep determination unit for one day. FIG. 5 illustrates the sleep state of the target person for one day, from 7 am in the morning to 6:59 the next morning. According to the present embodiment, the motion sensor 2 is disposed in a living room of the target person, and sleep is determined on the basis of the body motion data detected by the motion sensor 2. Therefore, the sleep determination unit 121 can determine not only whether the target person is asleep or awake but also whether the target person is in the room. However, when the target person is not in the room, the sleep determination unit 121 cannot determine whether the target person is asleep or awake.

In FIG. 5, the abscissa represents the time, and the ordinate represents whether the target person is sleeping ("asleep"), the target person who is awake is in the room ("in room (awake)"), or the target person is out of the room ("out of room"). The state "asleep", "in room (awake)", or "out of room" of the target person is indicated by each of a bar of the bar graph. If the target person is out of the room, the level of the bar is 0 (the lowermost level in FIG. 5). If the target person who is awake is in the room, the level of the bar is 1 (the mid-level in FIG. 5). If the target person who is sleeping is in the room, the level of the bar is 2 (the uppermost level in FIG. 5). Each bar of the bar graph is based on one minute, for example.

Figure 6:
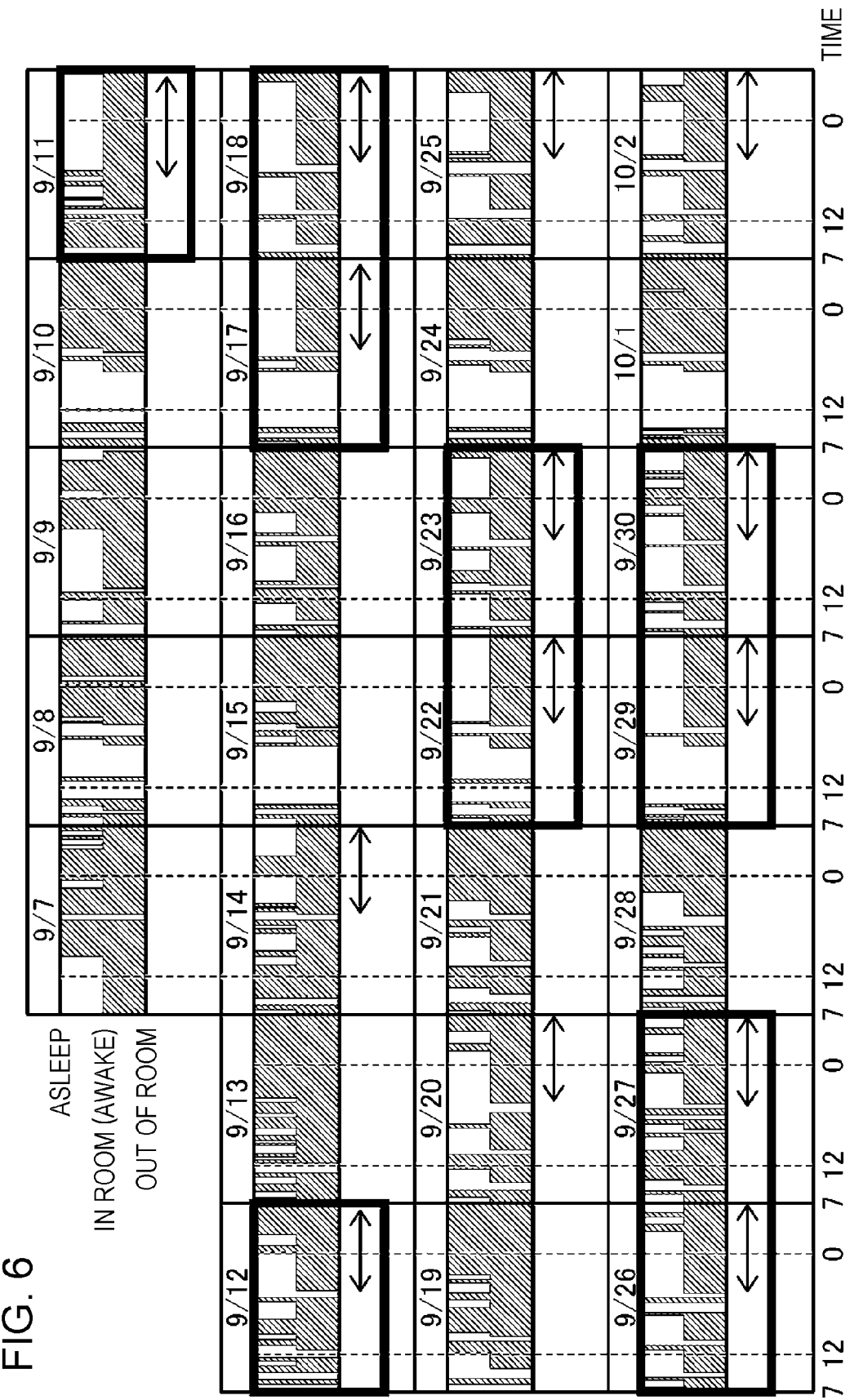
FIG. 6 illustrates an example of a sleep state for a predetermined time period output from the sleep determination unit.

FIG. 6 illustrates an example of the sleep state output from the sleep determination unit over a predetermined period of time. In FIG. 6, the sleep state of the target person from September 7 to October 2 of a certain year is illustrated. As can be seen from FIG. 6, at night on September 11, 12, 14, 17, 18, 20, 22, 23, 25, 26, 27, 29, and 30 and October 2, the target person has not enough sleep.

FIG. 7 illustrates an example of the physical condition data over a predetermined period of time. FIG. 7 illustrates the physical condition of the target person from September 7 to October 2 of the certain year. In FIG. 7, the circle indicates that the physical condition of the target person is good, and the cross mark indicates that the physical condition of the target person is bad. The sleep state illustrated in FIG. 6 and the physical condition illustrated in FIG. 7 are based on the data of the same target person. There is a correlation between the sleep state illustrated in FIG. 6 and the physical condition illustrated in FIG. 7, that is, a correlation that the sleep deprivation continues for two days before the physical condition deteriorates. For example, the target person has not enough sleep for 2 straight days (September 11 and 12), and the physical condition on September 13 (the following day) deteriorates.

As described above, the physical condition analysis unit 122 analyzes the physical condition data and the sleep state over a predetermined period of time. If sleep deprivation continues for two days before the physical condition deteriorates, the physical condition analysis unit 122 generates physical condition prediction information indicating that if sleep deprivation continues for two straight days, the physical condition of the following day deteriorates.

Figure 8:
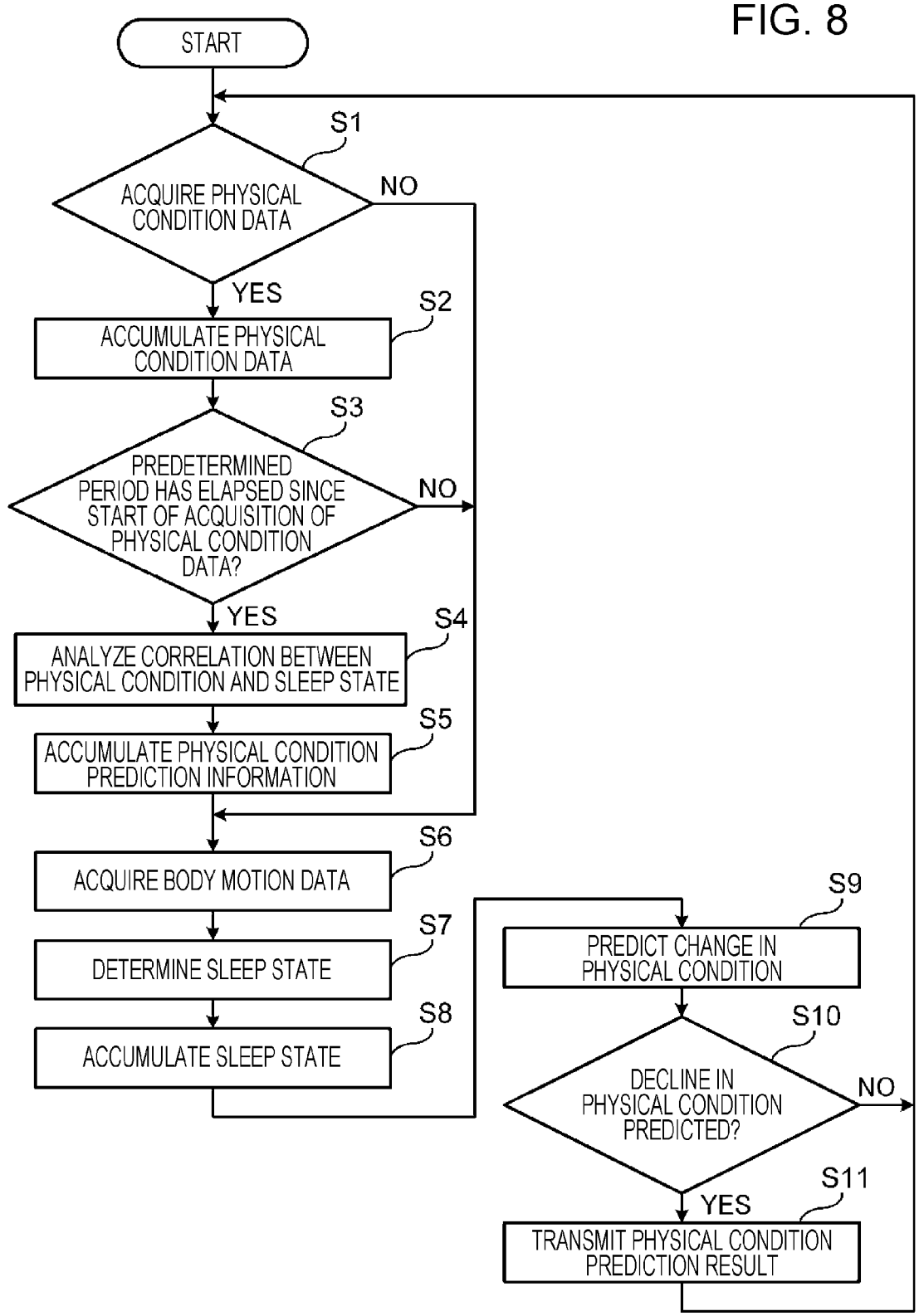
FIG. 8 is a flowchart of the operation performed by the server according to an embodiment.

FIG. 8 is a flowchart of the operation performed by the server according to the present embodiment.

In step S1, the physical condition data acquisition unit 112 determines whether the physical condition data indicating whether the physical condition of the target person is good has been acquired first. The physical condition data acquisition unit 112 receives the physical condition data transmitted from the terminal device 4. The physical condition data indicates, for example, whether the physical condition of the target person on the previous day is good. If it is determined that the physical condition data has not been acquired (NO in step S1), the processing proceeds to step S6.

However, if it is determined that the physical condition data has been acquired (YES in step S1), the physical condition data acquisition unit 112 accumulates the acquired physical condition data in the physical condition data accumulation unit 132 in step S2. Note that the physical condition data acquisition unit 112 may acquire physical condition data indicating the physical condition over one day or may acquire physical condition data indicating of physical condition over multiple days.

Subsequently, in step S3, the physical condition analysis unit 122 determines whether a predetermined period has elapsed since start of acquisition of the physical condition data of the target person. For example, the physical condition analysis unit 122 determines whether one month has elapsed since start of acquisition of the physical condition data of the target person. Note that the predetermined period is not limited to one month.

If it is determined that the predetermined period has not elapsed since start of acquisition of the physical condition data of the target person (NO in step S3), the processing proceeds to step S6.

However, if it is determined that a predetermined period has elapsed since start of acquisition of the physical condition data of the target person (YES in step S3), the physical condition analysis unit 122 analyzes a correlation between the physical condition of the target person and the sleep state of the target person over a predetermined time period in step S4. The physical condition analysis unit 122 generates the physical condition prediction information used to predict a change in the physical condition of the target person on the basis of the analysis result.

Subsequently, in step S5, the physical condition analysis unit 122 accumulates the generated physical condition prediction information in the physical condition prediction information accumulation unit 133.

If there is a correlation between the physical condition and the sleep state, a change in the physical condition can be predicted by using only the sleep state. Therefore, when the physical condition prediction information is accumulated in the physical condition prediction information accumulation unit 133, the physical condition data acquisition unit 112 may stop acquiring the physical condition data. In addition, if there is no correlation between the physical condition and the sleep state and, thus, the physical condition prediction information is not accumulated in the physical condition prediction information accumulation unit 133, the physical condition data acquisition unit 112 may stop acquiring the physical condition data.

Alternatively, if there is no correlation between the physical condition and the sleep state and the physical condition prediction information and, thus, the physical condition prediction information is not accumulated in the physical condition prediction information accumulation unit 133, the physical condition data acquisition unit 112 may resume acquiring the physical condition data, and the physical condition analysis unit 122 may increase the predetermined period of time. By increasing the predetermined period of time, the probability of finding a correlation between the physical condition and the sleep state can be increased.

Subsequently, in step S6, the body motion data acquisition unit 111 acquires the body motion data indicating the motion of the body of the target person.

Subsequently, in step S7, the sleep determination unit 121 determines the sleep state indicating whether the target person is asleep or awake on the basis of the body motion data acquired by the body motion data obtaining unit 111.

Subsequently, in step S8, the sleep determination unit 121 accumulates the determined sleep state of the target person in the sleep state accumulation unit 131.

Subsequently, in step S9, the physical condition prediction unit 124 predicts a change in the physical condition of the target person on the basis of the sleep state determined by the sleep determination unit 121 and the physical condition prediction information accumulated in the physical condition prediction information accumulation unit 133.

Subsequently, in step S10, the physical condition prediction unit 124 determines whether a decline in physical condition of the target person is predicted or not. If it is determined that a decline in physical condition of the target person is not predicted (NO in step S10), the processing returns to step S1.

However, if, in step S11, it is determined that a decline in physical condition of the target person is predicted (YES in step S10), the prediction result transmission unit 114 transmits, to the terminal device 4, the physical condition prediction result predicting a decline in physical condition of the target person. Thereafter, the processing returns to step S1.

As described above, the physical condition prediction system according to the present embodiment is capable of predicting a change in the physical condition of the target person on the basis of the constantly determined sleep state. In addition, since a change in the physical condition of the target person is predicted, the care plan for the target person who is an elderly or a dementia patient, for example, can be readjusted and, thus, the target person can be assisted more efficiently.

While the present embodiment has been described with reference to the physical condition prediction unit 124 that predicts a change in the physical condition of the target person when the sleep state is determined, the physical condition prediction unit 124 is not limited thereto. The physical condition prediction unit 124 may predict a change in the physical condition of the target person at a predetermined point in time. The predetermined point in time may be, for example, a point in time at 7 a.m. every day or may be predetermined intervals, such as 1-hour intervals. In this case, after the process of step S8, the physical condition prediction unit 124 determines whether the predetermined point in time is reached. If the physical condition prediction unit 124 determines that the predetermined point in time is reached, the processing may proceed to step S9. However, if the physical condition prediction unit 124 determines that the predetermined point in time is not reached, the processing may return to step S1.

According to the present embodiment, the physical condition prediction unit 124 may predict a decline in physical condition of the target person if the value of the body motion data falls below a predetermined value within a predetermined period of time.

Figure 9:
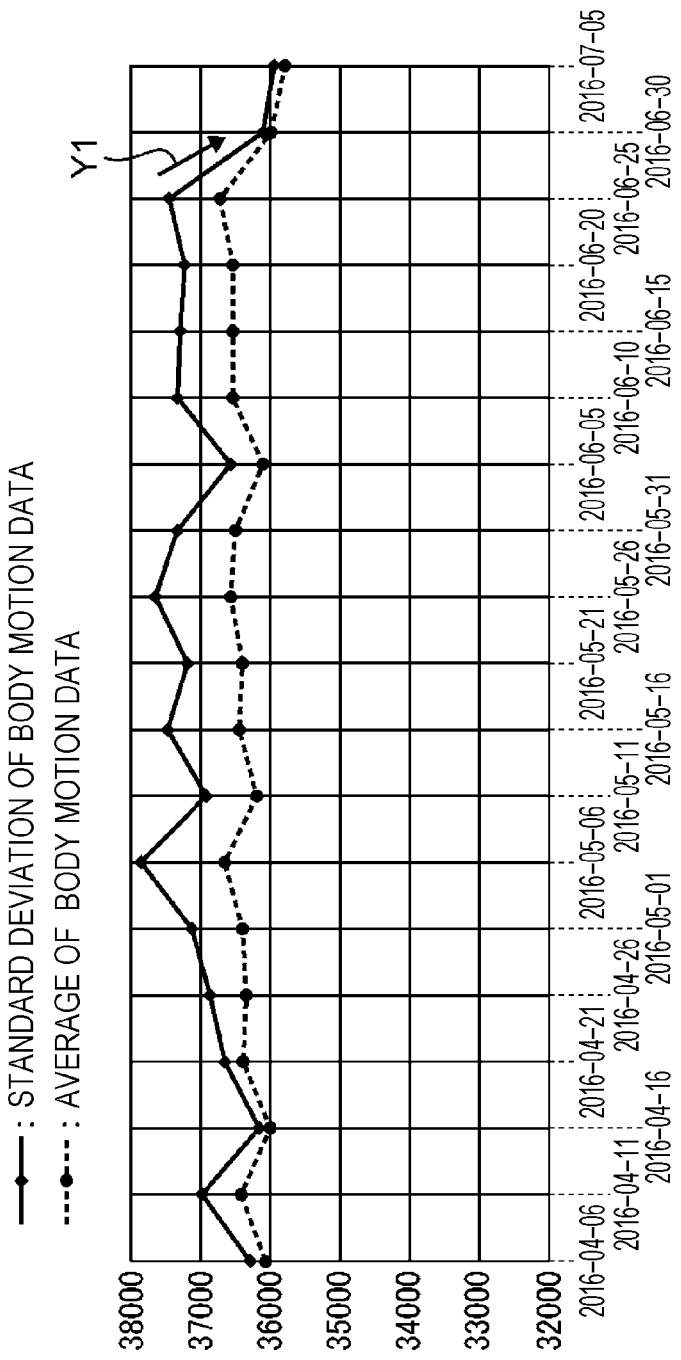
FIG. 9 illustrates an example of a history of the standard deviation and average value of body motion data.

FIG. 9 illustrates an example of the history of standard deviation and average value of the body motion data. In FIG. 9, the standard deviation and the average value of the body motion data of one day at 5-day intervals are illustrated. As indicated by an arrow Y1 in FIG. 9, when the standard deviation of the body motion data abruptly decreases within a predetermined period of time, the daily life activity (ADL) of the target person is reduced and, thus, the physical condition of the target person may deteriorate. Accordingly, the physical condition prediction unit 124 may predict a decline in physical condition of the target person if the value of the body motion data falls below a predetermined value within a predetermined period of time.

FIG. 10 illustrates the correlation between the onset of Behavioral and Psychological Symptoms of Dementia (BPSD) and the sleep state. In FIG. 10, the number of naps of the target person, the number of nocturnal awakening at night, the time of the occurrence of nocturnal awakening at night, and the night-time behavior are illustrated on a daily basis.

The sleep state is gathered in the sleep state accumulation unit 131 via the sleep determination unit 121. In addition, the physical condition data acquisition unit 112 extracts data corresponding to the symptoms of BPSD, such as wandering or delusions, from the nursing care record data and accumulates the extracted data in the physical condition data accumulation unit 132. The nursing care record data is input by, for example, a care giver of the target person.

As can be seen from FIG. 10, wandering, which is BPSD, occurs on May 21, and delusion, which is BPSD, occurs on May 22 and May 27. The physical condition analysis unit 122 analyzes the cause of the onset of BPSD on the basis of the onset of BPSD and the data accumulated in the sleep state accumulation unit 131. In this example, the following correlations are found: (1) On the day of the onset of BPSD, the number of nocturnal awakening is large; (2) On the day on which the number of nocturnal awakening is large, the number of naps during daytime or the number of naps in the evening is large. Accordingly, the following prediction can be derived: A nap during the daytime or a nap in the evening that cannot be controlled by a care giver leads to the onset of BPSD at night.

Therefore, the physical condition analysis unit 122 analyzes the correlation among the frequency of nocturnal awakening of the target person at night, the frequency of a nap of the target person during the daytime or the frequency of a nap in the evening, and the onset of behavioral and psychological symptoms of dementia of the target person. Subsequently, the physical condition analysis unit 122 generates the physical condition prediction information for predicting the onset of behavioral and psychological symptoms of dementia of the target person on the basis of the frequency of nocturnal awakening of the target person at night and one of the frequency of a nap of the target person during the daytime and the frequency of a nap in the evening. The physical condition prediction unit 124 predicts the onset of behavioral and psychological symptoms of dementia of the target person on the basis of the frequency of nocturnal awakening of the target person and the frequency of a nap of the target person during the daytime or in the evening.

Note that the physical condition prediction unit 124 may predict the occurrence of the behavioral and psychological symptoms of dementia of the target person on the basis of the frequency of nocturnal awakening of the target person at night. Alternatively, the physical condition prediction unit 124 may predict the occurrence of the behavioral and psychological symptoms of dementia of the target person on the basis of the frequency of a nap of a target person during daytime or in the evening. Still alternatively, the physical condition prediction unit 124 may predict the occurrence of the behavioral and psychological symptoms of dementia of the target person on the basis of at least one of the frequency of nocturnal awakening of the target person at night and the frequency of a nap of the target person during daytime or in the evening.

In this way, if the BPSD symptom and the sleep state are accumulated and analyzed by the physical condition analysis unit 122, the physical condition prediction unit 124 can predict whether the nighttime BPSD occurs in accordance with the state of a nap during daytime or in the evening. If the onset of BPSD can be predicted, the care giver can prepare for giving care to the target person, which may lead to reduction of work load imposed on the care giver. In addition, the care giver may eliminate events that cause the onset of BPSD of the target person.

While the above description has been given with reference to the case in which the onset of BPSD is predicted on the basis of only the sleep state, the present disclosure is not limited to the case. The activity amount of an elderly person can be determined on the basis of the body motion data, which are used to analyze the sleep state, and, thereafter, the correlation between the activity amount and BPSD can be analyzed. In addition, it is effective to combine various widely used vital sensors. The physical condition prediction unit 124 can predict the onset of BPSD on the basis of the correlation between a change in body temperature acquired by the infrared sensor or the temperature sensor and BPSD. In addition, the physical condition prediction unit 124 can predict the onset of BPSD on the basis of the correlation between the heart rate or respiration rate and BPSD by detecting the heart rate or respiratory rate from the body motion data.

In particular, in terms of heartbeat, a technique for evaluating the balance of autonomic nerves from heart rate variability is widely used. It is generally known that excessive stress conditions cause BPSD. Thus, if the degree of stress is detected from heartbeat and is applied, the accuracy of prediction of BPSD can be improved more.

In addition, for example, by combining living environment data (e.g., the indoor temperature, indoor humidity, illuminance, noise, and carbon dioxide concentration), a living environment which is a factor that causes a physical condition change or the onset of BPSD can be identified. In general, it is well known that the room temperature and the room humidity have an impact on a change in deep body temperature responsible for sleeping. Therefore, a factor that impairs sleep can be identified from the room temperature and the room humidity. The physical condition prediction unit 124 can predict a change in physical condition or the onset of BPSD on the basis of a correlation between a pair consisting of room temperature and the room humidity and one of a change in physical condition and BPSD. Similarly, a factor that impairs sleep can be further identified from noise or carbon dioxide concentration. The physical condition prediction unit 124 can predict a change in physical condition or the onset of BPSD on the basis of the correlation between one of noise and carbon dioxide concentration and one of a change in physical condition and BPSD.

While the apparatus according to the present disclosure has been described with reference to the embodiment above, the present disclosure is not limited to the embodiment. A variety of modifications of the present embodiment that are conceivable by those skilled in the art and an embodiment configured by combining constituent elements of different embodiments may be encompassed in the scope of one or a plurality of aspects of the present disclosure without departing from the spirit and scope of the present disclosure.

According to the above-described exemplary embodiment and each of the modifications, each of the constituent elements may be configured by using dedicated hardware or execution of a software program suitable for the constituent element. Each of the constituent elements may be realized by a program execution unit, such as a central processing unit (CPU) or a processor, reading out and executing a software program recorded on a recording medium, such as a hard disk or a semiconductor memory.

It should be noted that some or all of the functions of a device according to the embodiments of the present disclosure are typically implemented in the form of an LSI (Large Scale Integration), which is an integrated circuit. The functions may be formed as individual chips, or some or all of the functions may be integrated into a single chip. In addition, the circuit integration is not limited to LSI and may be achieved by dedicated circuitry or a general-purpose processor other than an LSI. A field programmable gate array (FPGA), which is programmable after fabrication of the LSI, or a reconfigurable processor which allows reconfiguration of connections and settings of circuit cells in LSI may be used.

In addition, some or all of the functions of the apparatus according to the embodiments of the present disclosure may be provided by a processor, such as a CPU, executing a program.

In addition, the numerical values used above are only illustrative examples for describing the technique of the present disclosure in detail, and the present disclosure is not limited to the examples of numeral values.

In addition, the order in which steps are executed described in the above-described flowchart are only illustrative example for describing the present disclosure, and the order may differ from that described above if the same effect can be obtained. Furthermore, some of the steps may be executed concurrently with other steps (in parallel).

Furthermore, a variety of modifications of each of the embodiments of the present disclosure that are conceivable by those skilled in the art without departing from the spirit and scope of the present disclosure are encompassed in the scope of the present disclosure.

What is claimed is:

1. A method comprising: continuously or intermittently acquiring, from a motion sensor, body motion data related to body motions of a target person, the motion sensor being configured to detect the body motions of the target person; generating, based on the acquired body motion data, sleep state data related to a sleep state of the target person; storing the generated sleep state data into a sleep state database; generating physical condition prediction information for the target person by collating (i) physical condition data for the target person, the physical condition data being a record of one or more changes in a physical condition of the target person over a predetermined period of time in a past and (ii) past sleep state data of the target person over the predetermined period of time in the past, wherein the physical condition prediction information for the target person is generated to indicate a correlation between (i) each of the one or more changes in the physical condition of the target person over the predetermined period of time in the past and (ii) the past sleep state data of the target person for a period of time prior to each of the one or more changes in the physical condition of the target person over the predetermined period of time in the past, wherein the past sleep state data is the sleep state data generated and stored in the sleep state database over the predetermined period of time in the past, and wherein the physical condition prediction information for the target person is unique to the target person; storing the generated physical condition prediction information into a physical condition prediction information database; predicting a future change in the physical condition of the target person based on (i) the generated sleep state data and (ii) the generated physical condition prediction information generated for the target person stored in the physical condition prediction information database; and, transmitting the predicted future change in the physical condition of the target person to a terminal configured to notify a care giver of the target person on the predicted future change in the physical condition of the target person.

2. The method according to claim 1, wherein: the body motion data indicate a number of the body motions of the target person per unit time detected by the motion sensor; the sleep state data indicate whether the target person is asleep or awake in each period; and the generating the sleep data includes determining that the target person is asleep when an evaluation value calculated from the body motion data over consecutive unit times is less than a predetermined value, and determining that the target person is awake when the evaluation value is greater than or equal to the predetermined value.

3. The method according to claim 1, wherein the physical condition data for the target person are input by an observer who observes the target person.

4. The method according to claim 1, wherein in the predicting the future change in the physical condition of the target person, the future change is predicted by pattern-matching (i) the generated sleep state data stored in the sleep state database with (ii) the past sleep state data of the target person correlated with each of the one or more changes of the physical condition of the target person in the generated physical condition prediction information for the target person stored in the physical condition prediction information database.

5. The method according to claim 1, further comprising: continuously or intermittently acquiring body temperature data indicating a body temperature of the target person, wherein the future change in the physical condition of the target person based on (i) the generated sleep state data, (ii) physical condition prediction information generated for the target person, and (iii) the body temperature data.

6. The method according to claim 1, wherein in the predicting the future change in the physical condition of the target person, the future change is predicted using a frequency of nocturnal awakening of the target person.

7. The method according to claim 1, wherein in the predicting the future change in the physical condition of the target person, the future change is predicted using an amount of time the target person is awake at night.

8. The method according to claim 3, wherein the physical condition data for the target person includes information about behavioral and psychological symptoms of dementia of the target person.

9. A computer comprising:
a processor; and
a memory that stores a program for causing the processor to execute the method according to claim 1.

10. A non-transitory storage medium storing a program that causes a processor to execute the method according to claim 1.

11. The method according to claim 1, wherein the motion sensor is a Doppler sensor configured to detect the body motions of the target person by emitting radio waves and comparing a frequency of the emitted radio waves with a frequency of reflected radio waves reflected from the target person.

12. The method according to claim 1, wherein the motion sensor is an acceleration sensor configured to detect the body motions of the target person by being worn on the body of the target person.

13. A method comprising: continuously or intermittently acquiring, from a motion sensor; body motion data related to body motions of a target person; the motion sensor being configured to detect the body motions of the target person; generating, based on the acquired body motion data, sleep state data related to a sleep state of the target person; storing the generated sleep state data into a sleep state database; generating physical condition prediction information for the target person by collating (i) one or more occurrences of behavioral and psychological symptoms of dementia of the target person over a predetermined period of time in a past and (ii) past sleep state data of the target person over the predetermined period of time in the past, wherein the physical condition prediction information for the target person is generated to indicate a correlation between (i) each of the one or more occurrences of the behavioral and psychological symptoms of dementia of the target person over the predetermined period of time in the past and (ii) the past sleep state data of the target person for a period of time prior to each of the one or more occurrences of the behavioral and psychological symptoms of dementia of the target person over the predetermined period of time in the past, wherein the past sleep state data is the sleep state data generated and stored in the sleep state database over the predetermined period of time in the past, and wherein the physical condition prediction information for the target person being unique to the target person; storing the generated physical condition prediction information into a physical condition prediction information database: predicting an onset of the behavioral and psychological symptoms of dementia of the target person by pattern matching (i) the generated sleep state data stored in the sleep state database with (ii) the past sleep state data of the target person correlated with each of the one or more occurrences of the behavioral and psychological symptoms of dementia of the target person in the generated physical condition prediction information for the target person stored in the physical condition prediction information database; and transmitting the predicted onset of the behavioral and psychological symptoms of dementia of the target person to a terminal configured to notify a care giver of the target person on the predicted onset of the behavioral and psychological symptoms of dementia of the target person.

14. A computer comprising:
   a processor; and
   a memory that stores a program for causing the processor to execute the method according to claim 13.

* * * * *